United States Patent [19]
Rosegay

[11] Patent Number: 5,240,915
[45] Date of Patent: Aug. 31, 1993

[54] AVERMECTIN DERIVATIVES

[75] Inventor: Avery Rosegay, Cranford, N.J.

[73] Assignee: Merck & Co., Inc., Rahway, N.J.

[21] Appl. No.: 776,120

[22] Filed: Oct. 15, 1991

[51] Int. Cl.$^5$ .................. C07H 17/08; C07D 493/22; A61K 31/70; A61K 31/365
[52] U.S. Cl. .................................. 514/30; 536/7.1; 549/264; 514/450
[58] Field of Search ............... 536/7.1, 18.5; 549/264, 549/265; 514/30, 450

[56] References Cited

U.S. PATENT DOCUMENTS

| | | | |
|---|---|---|---|
| Re. 32,006 | 10/1985 | Chabala et al. | 549/264 |
| Re. 32,034 | 11/1985 | Chabala et al. | 549/264 |
| 4,199,569 | 4/1980 | Chabala et al. | 514/30 |
| 4,200,581 | 4/1980 | Fisher et al. | 514/30 |
| 4,201,861 | 5/1980 | Mrozik et al. | 536/7.1 |
| 4,206,205 | 6/1980 | Mrozik et al. | 514/30 |
| 4,289,760 | 9/1981 | Mrozik et al. | 536/7.1 |
| 4,310,519 | 1/1982 | Albers-Schonberg et al. | 514/30 |
| 4,427,663 | 1/1989 | Mrozik | 514/30 |
| 4,457,920 | 7/1994 | Mrozik | 536/7.1 |
| 4,916,120 | 4/1990 | Röben et al. | 536/7.1 |
| 4,954,484 | 9/1990 | Gehret | 536/7.1 |

FOREIGN PATENT DOCUMENTS

214731 7/1986 European Pat. Off. .
276131 1/1988 European Pat. Off. .

OTHER PUBLICATIONS

Chen, et al. (I) Abstr. Pap. Am. Chem. Soc. 186 Mtg. MBTD 28, 1983.
Chen, et al (II) ARch. Biochem. Biophys 269 pp. 544–547 (1989).
Schulman, et al (II) J. Antibiotic 38, pp. 1494–1498 (1985).
Schulman, et al (II) Antimicrobial Agents & Chemo. 31 pp. 744–747 (1986).
Fisher, et al (II) Macrolide Antibiotics Omura, Ed. Aca. Press, NY 553–606 (1984).
Davies-Reid, et al J. Org. Chem. 53 pp. 923–925 (1988).B. Fraser-Reid et al. "Avermectin Chemistry", *J. Org. Chem.*, 53:4, pp. 923–925, 1988.
E. J. Corey et al. "Dimethyloxosulfonium Methylide and Dimethylsulfonium Methylide", *JACS* 87:6 pp. 1353–1364, 1965.
H. H. Szmant, *Organic Chemistry*, 1957.

*Primary Examiner*—Johnnie R. Brown
*Assistant Examiner*—Elli Peselev
*Attorney, Agent, or Firm*—David L. Rose; Joseph F. DiPrima

[57] ABSTRACT

There are disclosed avermectin derivatives which are avermectin modified at the 3- and 4-positions. The 3-hydroxy and 4-keto, epoxide and hydroxy (hydroxymethyl) derivatives and the 4-oxo compound are prepared from the natural avermectin by moving the 3,4-double bond exocyclic at 4 and forming a 3-hydroxy group. Osmolation gave an $\alpha,\beta$-diol across the double bond and cleavage of the diol provided the 4-oxo compound. The 4-oxo compound is epoxidized with an ylide reagent. The compounds are useful as anthelmintic agents and compositions for that use using the compounds as the active ingredient thereof are also described.

9 Claims, No Drawings

AVERMECTIN DERIVATIVES

BACKGROUND OF THE INVENTION

The term avermectin (previously referred to as C-076) is used to described a series of compounds isolated from the fermentation broth of an avermectin-producing strain of *Streptomyces avermitilis* and derivatives thereof. The morphological characteristics of the culture are completely described in U.S. Pat. No. 4,310,519. The avermectin compounds are a series of macrolides, each of which is substituted at the 13 position with a 4-(α-L-oleandrosyl)-α-L-oleandrose group. The avermectin compounds and the derivatives of this invention have a very high degree of anthelmintic and anti-parasitic activity.

The avermectin series of compounds isolated from the fermentation broth have the following structure:

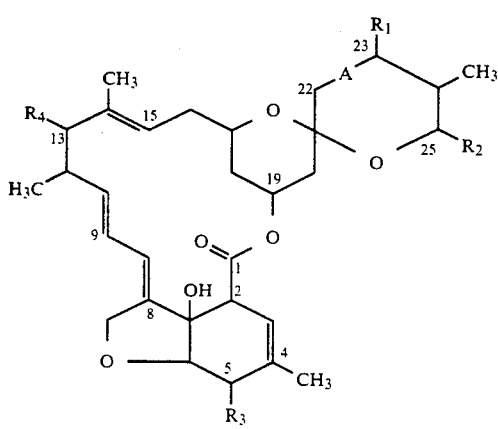

wherein $R_4$ is the 4'-(L-oleandrosyl)-α-L-oleandrosyloxygroup of the structure

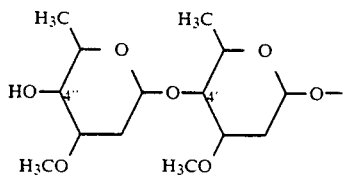

and wherein A at the 22,23 position indicates a single or a double bond; $R_1$ is a hydrogen or hydroxy and is present only when A indicates a single bond;

$R_2$ is iso-propyl or sec-butyl; and $R_3$ is methoxy or hydroxy.

There are eight different avermectin natural product compounds and they are given the designations A1a, A1b, A2a, A2b, B1a, B1b, B2a, and B2b based upon the structure of the individual compounds. In the foregoing structural formula, the individual avermectin compounds are as set forth below.

| (The R group is 4'α(L-oleandrosyl)α-L-oleandrosyloxy.) | | | |
|---|---|---|---|
| (A) | $R_1$ | $R_2$ | $R_3$ |
| A1a | double bond | — | sec-butyl | —OCH$_3$ |
| A1b | double bond | — | iso-propyl | —OCH$_3$ |
| A2a | single bond | —OH | sec-butyl | —OCH$_3$ |
| A2b | single bond | —OH | iso-propyl | —OCH$_3$ |
| B1a | double bond | — | sec-butyl | —OH |
| B1b | double bond | — | iso-propyl | —OH |
| B2a | single bond | —OH | sec-butyl | —OH |
| B2b | single bond | —OH | iso-propyl | —OH |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

In addition to these natural avermectins containing the 25-iso-propyl or 25-sec-butyl-substituent, closely related derivatives containing other branched or cyclic 25-alkyl or 25-alkenyl substituents, including those further substituted by heteroatoms such as oxygen, sulfur, nitrogen, and halogen, are known in the literature. These derivatives are obtained through various adjustments and additions to the fermentation procedures as described fully in the European Patent Application EPO 0 214 731.

Avermectins are products of microbial fermentations using the actinomycete *Streptomyces avermitilis*. These microbes use acetates and propionates as building blocks for most of the avermectin carbon chain, which is then further modified by microbial enzymes to give the completed avermectin molecules. It is known, however, that the carbon C-25 and the 2-propyl and 2-butyl substituents at this carbon are not derived from acetate or propionate units, but are derived from the amino acids L-valine and L-isoleucine, respectively. It was reasoned that these amino acids are deaminated to the corresponding 2-ketoacids, and that these then are decarboxylated to give 2-methylpropionic and 2-methylbutyric acids. These acids then have been found to be directly incorporated into the avermectin structures to give the 2-propyl and 2-butyl C-25 substituents, as is reported by Chen et al., *Abstr. Pap. Am. Chem. Soc.* (186 Meet., MBTD 28, 1983). It was also disclosed in European Patent Application number 0 214 731 that additions of large amounts of other acids such as cyclopentanoic, cyclobutyric, 2-methylpentanoic, 2-methylhexanoic, thiophene-3-carboxylic acids and others to the fermentation broth of *S. avermitilis* causes the microbes to accept these acids as substitutes and to make small amounts of avermectins containing these acids in form of new C-25 substituents. Examples of such new avermectin derivatives are:

25-(thien-3-yl)-25-de-(1-methylpropyl)avermectin A2a
25-(cyclohex-3-enyl)-25-de-(1-methylpropyl)avermectin A2a
25-cyclohexy-25-de-(1-methylpropyl)avermectin A2a
25-(1-methylthioethyl)-25-de-(1methylpropyl)avermectin A2a
25-(2-methylcyclopropyl)-25-de-(1-methylpropyl)avermectin A2a.

Similar experiments producing avermectins "c" and "d" containing as C-25 substituents a 2-pentyl and 2-hexyl group are described by T. S. Chen et al. in *Arch. Biochem. Biophys.* 1989, 269, 544–547.

Still additional avermectin derivatives are produced through artificial modification of the fermentation of *Streptomyces avermitilis* either by addition of metabolic inhibitors such as sinefungin (as described by Schulman et al., *J. Antibiot.* 1985, 38, 1494–1498) or by mutation of the parent strain (as described by Schulman et al., *Antimicrobial Agents and Chemotherapy*, 1987, 31, 744–747, and by EP-276-131-A to Pfizer INC.). Some of these avermectin derivatives are still further modified and are missing one or two of the 3′- and 3″-O-methyl groups (Schulman et al., *J. Antibiot.* 1985, 38, 1494–1498).

The fermentation products have been chemically modified in order to obtain further antiparasitic and insecticidal analogs with improved properties. Publications of such procedures in the scientific and patent literature have been reviewed by Fisher, M. H.; Mrozik, H.; in *Macrolide Antibiotics*; Omura, S., Ed.; Academic: New York, 1984; pp. 553–606, and by Davies, H. G.; Green, R. H. *Nat. Prod. Rep.*, 1986, 3, 87–121.

For example, a group of semisynthetic avermectin derivatives were obtained by hydrogenating specifically the 22,23-double bond of avermectin B1 giving 22,23-dihydroavermectin B1 derivatives which have very potent anthelmintic and antiparasitic properties. Other examples of semisynthetic avermectin derivatives contain a 8,9-oxide group, a 4a-hydroxy or acyloxy group, a 23-keto group, which all are potent antiparasitic and insecticidal compounds.

It has also been described by Mrozik in U.S. Pat. No. 4,427,663 that amino substituents at the 4″- and 4′-positions have very high antiparasitic and insecticidal activities.

These compounds may be used as starting materials for the compounds of this invention without further modification, or when containing additional reactive groups, which are not to be modified under the reaction conditions applied, only after protection of such with a suitable protecting group.

SUMMARY OF THE INVENTION

The instant invention is concerned with novel avermectin derivatives, specifically those derivatives which are modified at the 3- and 4-positions. Specifically 3-hydroxy and 4-oxo, 4-epoxide, 4,4 a dihydroxy and the 4-oxo compounds are prepared. The compounds are prepared by the oxidation of the known 3-hydroxy 4-exomethylene compound. Thus, it is an object of this invention to describe such compounds. It is a further object of this invention to describe processes for the preparations of such compounds. It is a further object of this invention to describe a series of process steps which enables the preparations of avermectin compounds with a radio-active carbon label at the 4a-position. A still further object of this invention is to describe the use of such compounds as anthelmintic agents. A still further object is to describe compositions containing such compounds as the active ingredient thereof. Further objects will be apparent from a reading of the following description.

DESCRIPTION OF THE INVENTION

The compounds of the instant invention are best realized in the foregoing structural formula:

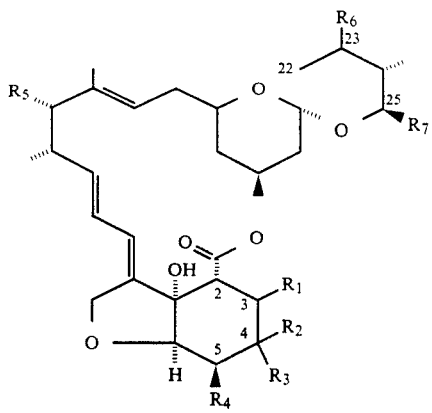

where $R_1$ is hydroxy or loweralkanoyloxy;
$R_2$ is hydroxy or loweralkanoyloxy and $R_3$ is hydroxymethyl or loweralkanoyloxy methyl; or
$R_2$ and $R_3$ together represent oxo or an epoxide;
$R_4$ is hydroxy, loweralkoxy, loweralkanoyl, oxo or oximino;
$R_5$ is hydrogen, hydroxy,

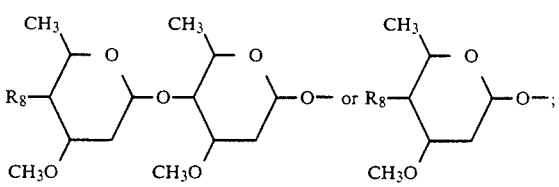

where $R_8$ is hydroxy, oxo, amino or mono- or disubstituted amino where the substituents are loweralkyl or loweralkanoyl;
$R_6$ is hydrogen, hydroxy or oxo and the broken line at the 22,23-position indicates a 22,23-single bond or the broken line at 22,23 indicates a 22,23-double bond and $R_6$ is not present; and
$R_7$ is loweralkyl or loweralkenyl or cycloloweralkyl.

The term "loweralkyl" as used in the instant applications is intended to include those alkyl group at from 1 to 6 carbon atoms of either a straight or branched chain configuration. Examples of such alkyl groups are methyl, ethyl, propyl, isopropyl, butyl, tertiary butyl, pentyl, isopentyl, hexyl and the like.

The term "loweralkoxy" is intended to include those alkoxy groups of from 1 to 6 carbon atoms of either a straight or branched configuration. Examples of such alkoxy groups are methoxy, ethoxy, propoxy, isopropoxy, butoxy, secondary butoxy, pentoxy, hexoxy and the like.

The term "loweralkanoyl" is intended to include those alkanoyl groups of from 1 to 6 carbon atoms of either a straight or branched configuration. Examples of such alkanoyl groups are formyl, acetyl, propionyl, butyryl, isobutyryl, pentanoyl, hexanoyl, and the like.

Preferred compounds of the instant invention are realized in the foregoing structural formula wherein $R_1$ is hydroxy;
$R_2$ is hydroxy and $R_3$ is hydroxy methyl; or
$R_2$ and $R_3$ together represent oxo or an epoxide;
$R_4$ is hydroxy, loweralkoxy, oxo or oximino;
$R_5$ is hydrogen, hydroxy, or

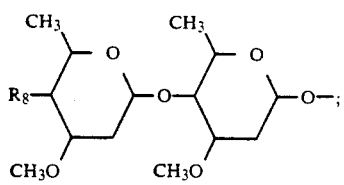

where $R_8$ is hydroxy, amino or mono- or di-substituted amino when the substituents are lower alkyl or lower alkanoyl;

$R_6$ is hydrogen or hydroxy and the broken line at 22,23- represents a 22,23-single bond; and $R_7$ is lower alkyl.

Further preferred compounds of the instant invention are realized in the foregoing structure wherein $R_1$, $R_2$ and $R_3$ are as defined above;

$R_4$ is hydroxy, methoxy or oximino;

$R_5$ is

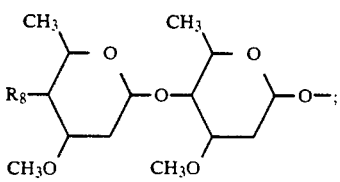

$R_8$ is hydroxy, amino, methylamino or acetylamino;

$R_6$ is as defined above; and $R_7$ is isopropyl or sec-butyl.

The compounds of the instant invention are prepared by the process outlined in the following reaction scheme wherein, for simplicity, only carbon atoms 2 through 7 are shown:

REACTION SCHEME

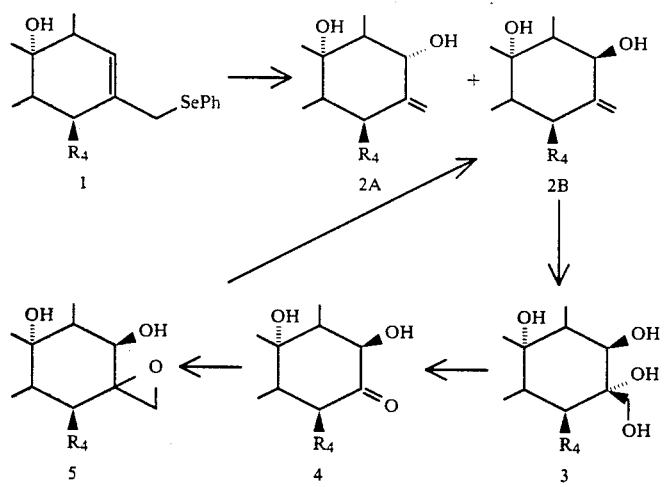

In the foregoing Reaction Scheme, compounds 1, 2A and 2B and the preparation thereof are disclosed in Fraser-Reid et. al. *J. Org. Chem.*, 53, pg 923–925 (1988).

The immediate starting material for the compounds and process of this invention are prepared by the procedures described in Fraser-Reid et al supra where the 4a-methyl group is substituted with a phenylseleno group using N-(phenylseleno) phthalimide to prepare Compound 1 in the Reaction Scheme. This compound, after suitable protection, is treated with hydrogen peroxide in pyridine to prepare the stereoisomeric pair 2A and 2B.

The 3β-hydroxy compound, 2B, is only used with the next step of the reaction schemes because the 3α-stereochemistry of 2A prevents the proper reaction to compound 3. The reaction of compound 2B to compound 3 is accomplished with an oxidizing reagent, preferably osmium tetroxide. Other oxidizing reagents have been tried such as permanganate, but osmium tetroxide has been found to be superior. The reaction is carried out in a nonpolar solvent preferably a hydrocarbon such as benzene or toluene. Benzene is preferred. The reaction is carried out preferably at room temperature and is complete in from 5 minutes to 5 hours. Higher temperature, up to 50° C. will reduce the reaction time somewhat.

The trihydroxy compound 3 is treated with lead acetate in a hydrocarbon solvent such as benzene or toluene at a reaction temperature of from 20° to 60° C., preferably about 40°–50° C. to prepare the 4-oxo compound (4). The reaction is very fast and is generally complete as soon as the lead tetracetate is added to the starting material solution. The reaction may be followed chromatographically to determine that the reaction is complete.

Compound 4 is then treated with a methylenating ylide reagent. Several such reagents are available however, the methylated ylide from dimethylsulfoxide (See Example 6) has been found to be very simple to prepare and the best reagent for introducing radioactive carbon to the molecule. The ylide reagent is prepared as described in Corey et al *JACS* 86 pg. 1353 (1965). The reaction with the 4-oxo compound is carried out in an inert solvent such as methylene chloride, chloroform, THF, ether and the like, preferably methylene chloride, at room temperature. The reaction is very simple and is generally complete in from 10 minutes to 1 hour.

Compound 5 in then reconverted to compound 2B, except for the presence of a radiolabeled carbon atom at the 4-position by using an epoxide deoxygenating reagent such as 3-methylbenzothiazole-2-selone. The reaction is carried out in an inert solvent, preferably a hydrocarbon such as benzene at room temperature and is complete in for 5 to 20 hours.

The 4-methylene reagent, compound 2B, now with a radiolabel at the 4-methylene can be converted back to the avermectin structure without the 3-hydroxy by following the procedures of Fraser-Reid et al. Generally the procedure involves the preparation of the methanesulfonyl derivative of the 3-hydroxy, the bromination of the 4-methylene which simultaneously cleaves the methanesulfornyloxy group and forms the 4,5-double bond. The 4a-bromo can then be cleaved being the normal avermectin structure with the correct stereochemistry and radiolabeled at the 4a methyl group.

It is noted that in the foregoing Reaction Scheme, the process proceeds from Compound 2B to Compound 5 and then back to Compound 2B. This circular process has advantages because in Compound 2B the carbon atom at 4a, the exomethylene carbon atom, at the start of the process, is not the same 4a carbon atom at the end of the process. This process thus allows the 4a carbon to be changed to a radioactive carbon atom such as isotopic $^{13}C$ or radioactive $^{14}C$. The original 4a-carbon atom would have been synthesized during the natural fermentation process that originally prepared the avermectin carbon atom and the specific inclusion of a radioactive carbon atom at a particular site would have been impossible. The specific inclusion of radioactive carbon atoms in the avermectin molecule is very important in carrying out studies to determine the fate of the molecule when it is administered to a living animal or when it is applied to plants, soils or aquatic environments. Thus, an aspect of this invention is the process of incorporating a radioactive carbon atom specifically into the 4a position of the avermectin molecule.

In addition, however, all of the compounds and derivatives thereof, that are prepared as intermediates in the cyclic process from compound 2B and back again to compound 2B are unique avermectin compound and active anthelmintic agents.

PREPARATION OF STARTING MATERIALS

The ultimate starting materials for the compounds of this invention are the avermectin fermentation products defined above which have the isopropyl or sec-butyl group at the 25-position. Thus it is apparent that additional reactions are required to prepare many of the immediate starting materials for the instant compounds. Specifically, reactions are carried out at the 4', 4", 5', 13, and 23 positions. In addition, during the various reactions described above, and below it may be necessary to protect various reactive groups to prevent the undesired reaction of such groups. In addition, protection of such reactive groups may facilitate the separation of the various products. Following the described reactions, the protecting groups may be removed and the unprotected product isolated. The protecting group employed is ideally one which may be readily synthesized, will not be affected by the reaction with the various reagents employed and may be readily removed without affecting any other functions of the molecule. It is noted that the instant protected compounds are novel and have considerable antiparasitic activity. They are included within the ambit of the instant invention. One preferred type of protecting group for the avermectin type of molecule is the tri-substituted silyl group, preferably the trialkyl silyl group. One especially preferred example, is the t-butyl dimethylsilyl group. The reaction preparing the protected compound is carried out by reacting a hydroxy compound with the appropriately substituted silylhalide, preferably the silylchloride in an aprotic polar solvent such as dimethylformamide. Imidazole is added as a catalyst. The reaction is complete in from 1 to 24 hours at from 0° to 25° C. For the 5-position hydroxy group the reaction is complete in from ½ to 3 hours at from 0° C. to room temperature. This reaction is selective to the 5 position under the conditions above described and very little, if any, silylation is observed at other hydroxy substituted positions.

The silyl groups are then removed after the other reactions have been carried out. The silyl group or groups are removed by stirring the silyl compound in methanol catalyzed by a catalytic amount of an acid, preferably a sulfonic acid such as p-toluene sulfonic acid. The reaction is complete in about 1 to 12 hours at from 0° to 50° C. Alternatively, the silyl group or groups can be removed with a hydrogen fluoride-pyridine complex in an organic solvent such as tetrahydrofuran. The reaction is complete in from about 3 to 24 hours and is preferably carried out at room temperature.

Additional reactions which may be carried out to prepare the compounds of this invention are the selective removal of one of the α-L-oleandrosyl moieties (described in U.S. Pat. No. 4,206,205 to Mrozik et al.).

The reaction conditions which are generally applicable to the preparation of both the mono-saccharide and aglycone involve dissolving the avermectin compound or the hydrogenated avermectin compound in an aqueous acidic non-nucleophilic organic solvent, miscible with water, preferably dioxane, tetrahydrofuran, dimethoxyethane, dimethylformamide, bis-2-methoxyethyl ether, and the like, in which the water concentration is from 0.1 to 20% by volume. Concentrated sulfuric acid is added to the aqueous organic solvent to the extent of 0.01 to 10% by volume. The reaction mixture is generally stirred at about 20°–40° C., preferably at room temperature, for from 6 to 24 hours. The lower concentration of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The products are isolated, and mixtures are separated by techniques such as column, thin layer preparative and high pressure liquid chromatography, and other known techniques.

The acids which may be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the monosaccharide or aglycone of the avermectin compounds or of the hydrogenated avermectin compounds utilizes a different solvent system for the mono-saccharide and the aglycone. The procedure for the preparation of the monosaccharide uses 1% acid by volume in isopropanol at from 20°–40° C., preferably room temperature, for from 6 to 24 hours. For the preparation of the aglycone, 1% acid, by volume, in methanol under the foregoing reaction conditions has been found to be appropriate.

Any strong inorganic or organic acid is appropriate for this process, and again sulfuric acid is the preferred acid.

It has also been observed that the mono-saccharide is prepared during the course of the reaction used to remove the trialkylsilyl protecting group. Since acid catalysis is used to remove the protecting group, this is expected. However, in such cases, both the desired product and the monosaccharide are prepared and they can be readily separated using the above-described techniques.

The 4''-, 4'-, 13- and/or 23-hydroxy groups are oxidized to the 4''-, 4'-, 13- and/or 23-keto groups respectively using oxidizing agents such as pyridinium dichromate; oxalylchloride-dimethylsulfoxide; acetic anhydride-dimethylsulfoxide; chromic acid-dimethylpyrazole; chromic acid; trifluoromethylacetic anhydride-dimethylsulfoxide; chromic acid-acetic acid; and the like. Oxalylchloride-dimethylsulfoxide (Swern oxidation) is the preferred oxidizing method. Suitably protectd compounds, as described above, are employed. The reaction is carried out at from dry-ice bath temperatures to room temperature, preferably from dry-ice bath temperatures to 0° C., and is complete in from 1-24 hours. The reaction may be carried out in any solvent in which the starting materials are reasonably soluble, and which will not react with the oxidizing agent. Such solvents as dimethylformamide, dimethylsulfoxide, methylene chloride, chloroform, carbon tetrachloride and the like are acceptable. For pyridinium dichromate reactions, dimethylformamide and dimethylsulfoxide are preferred. For chromic acid-dimethylpyrazole reactions, methylene chloride is preferred. The compounds are isolated from the reaction mixture using procedures known to those skilled in the art.

The 4' or 4''-keto compound is aminated to prepare the unsubstituted amino compound as described in U.S. Pat. No. 4,427,663 to Mrozik. The reaction is carried out in an inert solvent such as methanol at from −10° to +25° C. using ammonium salts and sodium cyanoborohydride as the aminating and reducing reagents, respectively. The reaction is complete in from 15 minutes to 24 hours and the product 4''-deoxy-4''-amino compound is isolated using techniques known to those skilled in the art. Suitable ammonium salts are the acetate, propionate, benzoate and the like. The acetate is preferred.

As a variation to the foregoing amination reaction, methyl ammonium salts can be used in place of the ammonium salts to prepare the monomethyl substituted compound directly. The same reagents, salts and reaction conditions as described above can be used for such a reaction.

The substitution reaction wherein the substituent on the various hydroxy groups or on the 4''-amine is an acyl function is carried out using an acylating reagent in the presence of a base in an inert solvent. The acylation of avermectin compounds, is fully described in U.S. Pat. No. 4,201,861 to Mrozik et al. THe preferred acylating reagents are loweralkanoyl anhydrides, loweralkanoyl halides, substituted benzene sulfonyl chlorides, lower alkyl sulfonyl chlorides, and the like. The reaction is carried out in an inert solvent such as methylene chloride in the presence of a non-reactive base such as pyridine or triethylamine in order to neutralize the acid produced during the course of the reaction. The reaction temperature is from −10° to 25° C. and the reaction is complete in from 5 minutes to 8 hours. The product is isolated using known techniques.

The reaction for the preparation of the 4'-or 4''-deoxy-4'- or 4''-dialkylamino compounds is carried out using the alkylating reaction conditions of an excess of a carbonyl compound, preferably formaldehyde and a reducing agent such as sodium cyano borohydride, in methanol. The reaction is carried out in a solvent suitable to dissolve the organic starting material using excess aqueous formaldehyde along with the presence of a small amount of acid such as acetic acid to facilitate the reaction. The reaction is carried out at from −10° to +25° C. with the solution of the avermectin compound in methanol added dropwise over a period of from 30 to 60 minutes to the alkylating reagent mixture and the product is isolated using known techniques.

Further reactions of the avermectin compounds are possible to prepare the compounds of this invention.

Following the preparation of the aglycone ($R_5$ is hydroxy at the 13 position), U.S. Pat. Nos. Re. 32,006 and Re. 32,034 to Chabala et al. disclose the hydroxy group displacement with a halogen using a reagent such as benzene sulfonylhalide, and the halogen is removed by reduction using a reducing agent such as trialkyltin hydride.

The hydroxy group at 5 may be alkylated following the procedures described in U.S. Pat. No. 4,200,581 to Fisher et al.

Another of the starting materials used in the foregoing reaction scheme are those in which the 22,23 double bond of the "1" type compounds has been reduced to a single bond. As is readily apparent from an analysis of the structure of avermectin starting materials there are 5 unsaturations in the 1-series of compounds. Thus in the 1-series of compounds it is necessary to reduce the 22,23 double bond while not affecting the remaining four unsaturations or any other functional group present on the molecule in order to selectively prepare the 22,23 dihydro avermectins. It is necessary to select a specific catalyst for the hydrogenation, one that will selectively hydrogenate the least hindered from among a series of unsaturations. The preferred catalyst for such a selective hydrogenation procedure is one having the formula:

$$[(R_9)_3P)_3RhY)]$$

wherein:

$R_9$ is loweralkyl, phenyl or loweralkyl substituted phenyl and Y is halogen. The reduction procedure is completely described in U.S. Pat. No. 4,199,569 to Chabala et. al.

The instant compounds are potent endo-and ecto-antiparasitic agents against parasites particularly helminths, ectoparasites, insects, and acarides, infecting man, animals and plants, thus having utility in human and animal health, agriculture and pest control in household and commercial areas.

The disease or group of diseases described generally as helminthiasis is due to infection of an animal host with parasitic worms know as helminths. Helminthiasis is a prevalent and serious economic problem is domesticated animals such as swine, sheep, horses, cattle, goats, dogs, cats, fish, buffalo, camels, llamas, reindeer, laboratory animals, furbearing, animals, zoo animals and exotic species and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Copperia, Ascaris, Bunstomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoma, Unciniaria, Toxascaris and Parascaris. Certain of these, such as Nematodirsu, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs and cats, Nematospiroides, Syphacia, Aspiculuris in rodents, arthropod ectoparasites of animals and birds such as ticks, mites, lice, fleas, blowflies, in sheep Lucilia sp., biting insects and such migrating dipterous larvae as Hypoderma sp. cattle, Gastrophilus in horses, and Cuterebra sp. in rodents and nuisance flies including blood feeding flies and filth flies.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly *Musca domestica* as well as fleas, house dust mites, termites and ants.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acerage infested with fire ant nests. The compounds are scattered above the infested area in low levels in bait formulations which are broght back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally indlucing one or more additiona active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area application, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or owther arthropod pests.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting arthropods in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired anti-parasitic result.

In using the compounds of this invention, the individual compounds may be prepared and used in that form. Alternatively, mixtures of the individual compounds may be used, or other active compounds not related to the compounds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

EXAMPLE 1

4a-Phenylseleno avermectin B1

A solution of 11.6 of 4a-hydroxy avermectin B1a/B1b (See U.S. Pat. No. 4,457,920 to Mrozik) in 70 mL of methylene chloride under nitrogen is cooled to −20° C. and combined with 9.0 mL of tri-n-butylphosphine and 8.0 g of N-(phenylseleno)phthalimide. The reaction mixture is stirred for 1 hour, the solvent is evaporated in vacuo, the residue is combined with 100 mL of ether-hexane 1:1 and the precipitate of phthalimide is removed by filtration. The ether-hexane is evaporated in vacuo and the product is chromatographed on a silica gel column using 2% methanol in methylene chloride as eluant. Evaporation of the solvent in vacuo affords 13.1 g of the phenylselenide which is 92% pure by HPLC analysis. The product is identified by nuclear magnetic resonance and mass spectrometry as 4a-phenylseleno avermectin B1a/B1b.

EXAMPLE 2

4a-Phenylseleno-4",5-bis-O-tert-butyl dimethylsily 7-O-trimethylsilyl avermectin B1

A solution of 13.1 g of the product of Example 1 and 5.2 g of imidazole in 100 mL of dry dimethylformamide is combined with 7.7 g of tert-butyldimethylsilyl chloride and stirred at room temperature for 24 hours. The resulting solution of 4 is then combined with 10 mL of bis(trimethylsilyl)trifluoroacetamine, stirred for 4 hours, combined with 200 mL of ethyl acetate, and washed 4 times with 100 mL of water. The ethyl acetate layer is dried over sodium sulfate, evaporated in vacuo, and the residue is combined with 100 mL of ethyl acetate-hexane 1:7 and clarified by filtration. The product obtained upon solvent evaporation is chromatographed on a silica gel column using a gradient of 5% to 15% ethyl acetate in hexane to afford 2.2 g of the title compound identified by nuclear magnetic resonance and mass spectrometry.

EXAMPLE 3

3-Hydroxy-4-methylene 4",5-bis-O-tert-butyldimethylsilyl-7-O-trimethylsilyl avermectin B1a A solution of 2.2 g of the product of Example 2 in 30 mL of pyridine is cooled in an ice bath and 3.0 mL of 30% hydrogen peroxide is added with stirring continued for 1 hour. 100 mL of ether is added, and the solution is washed several times with water and repeatedly with 0.05N hydrochloric acid until free of pyridine, and finally with water to neutrality. The ether is dried over magnesium sulfate, evaporated, and the product is chromatographed on a silica gel column using a gradient of 5% to 15% ethyl acetate in hexane as eluant. The fractions are monitored by silica gel thin layer chromatography using hexane-tetrahydrofuran 3:1 as the developing solvent. The product fractions are combined and evaporated to afford 1.2 g of the title compound as a mixture of approximately 3 parts 3B-hydroxy and 1 part 3α-hydroxy compound identified by nuclear magnetic resonance and mass spectrometry.

EXAMPLE 4

3β,4α,4a trihydroxy 4'',5-bis-O-tert-butyldimethylsilyl 7-O-trimethylsilyl avermectin B1

100 mg of the 3β-hydroxy compound of Example 3 is dissolved in 2 mL of pyridine and 0.1 mL of a 1.0M solution of sodium tetroxide in benzene is added. After stirring for 1 hour at room temperature, 1.5 mL of a 0.4M solution of sodium bisulfate in pyridine-water 40:60 is added and stirring is contained for 4 hours. The mixture is combined with 20 mL of ether, washed several times with water, dried over magnesium sulfate, and the ether evaporated in vacuo. The product is chromatographed on 2 silica gel preparative chromatography plates 0.5 mm thick using hexane-THF 3:1 as the developing solvent. The product bands are eluted with ethanol-ethyl acetate 1:5 to afford 51 mg of the title compound which is identified by nuclear magnetic resonance and mass spectrometry.

EXAMPLE 5

3β-Hydroxy-4-oxo-4'',5-bis-O-tertbutyldimethylsilyl-7-O-tri-methylsilyl avermectin B1

400 mg of the product of Example 4 in 5 mL of benzene is stirred in a bath at 50° C., and a 0.05M solution of lead tetracetate in benzene is added dropwise while monitoring the reactions by HPLC for unreacted 1. 30 mL of ether is added, the ether solution is washed several times with water, dried over sodium sulfate, and the product is purified by preparative thin layer chromatography in hexane-tetrahydrofuran 3:1. Elution with 5% ethanol in ethylacetate afforded 220 mg of the title compound, identified by nuclear magnetic resonance and mass spectrometry.

EXAMPLE 6

Preparation of labeled Methylenating Reagent

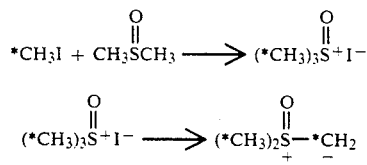

The carbon isotope (*) is introduced into reagent 6a by the procedure of E. J. Corey, et al JACS 86 1353 (1965).

The isotopic methylenating reagent 6b is prepared by combined 264 mg of 6a, 132 mg of 18-crown-6, 120 mg of potassium tert-butoxide and 5 mL of tetrahydrofuran and stirring the mixture at room temperature for 3 hours. On standing, the salts settle out, and assay of the supernatant indicated a 0.16M solution of 6b.

EXAMPLE 7

3β-Hydroxy 4,4a epoxide 4'',5-bis-O-tertbutyldimethylsilyl-7-O-trimethylsilyl avermectin B1

36 mg of the product of Example 5 in 4 mL of methylene chloride is combined with 0.2 mL of a 0.16M solution of the reagent 6b prepared in Example 6 in tetrahydrofuran and stirred for 30 minutes. Analysis by HPLC indicated an equal mixture of the epimeric and 4,4a epoxides. Ether was added and the solution was washed with 0.05N acetic acid, several times with water, dried over sodium sulfate and concentrated to a small volume. The product was flash chromatographed on a column of 1 g of silica gel using ether as eluant. Evaporation of the solvent afforded 27 mg of a mixture of the title compound, identified by nuclear magnetic resonance and mass spectrometry.

EXAMPLE 8

3β-Hydroxy-4-methylene-4'',5-bis-O-tertbutyldimethylsilyl-7-O-trimethylsilyl avermectin B1

A solution of 27 mg of epoxides the product of Example 8, 25 mg of 3-methylbenzothiazole-2-selone and 5 μL of trifluoroacetic acid is kept at room temperature for 13 hours, whereupon analysis by HPLC indicate complete conversion to the 4-exomethylene compound. Ether is added, the solution is washed several times with water, dried over sodium sulfate, and evaporated to a small volume. The product is isolated by HPLC on a Vydac C18 semi-preparative column using methanol-acetonitrile-water 30:65:5 as eluant and UV monitoring at 245 nm. The combined product fractions are evaporated in vacuo below 40° C. to afford the title compound, identified by nuclear magnetic resonance and mass spectrometry. The product is chromatographically identical to the product of Example 3 by HPLC and by silica gel thin layer chromatography.

EXAMPLE 9

3-Methane sulfonyloxy-4-methylene-4'',5-bis-O-tert-butyl di-methylsilyl-7-O-trimethylsily avermectin B1

A solution of 36 mg of the product of Example 8 in 4 mL of methylene chloride at 0° C. is combined with 1 mg of dimethylaminopyridine, 0.1 mL of triethylamine and 7.0 μL of methanesulfonylchloride. The mixture is stirred for 5 minutes, 1.0 mL of saturated sodium bicarbonate solution is added, the organic layer is washed several times with water, dried over sodium sulfate and concentrated to a small volume. The product is chromatographed on silica gel to afford 26 mg of the title compound, identified by nuclear magnetic resonance and mass spectrometry.

EXAMPLE 10

4a-Bromo-4'',5-bis-O-tert butyl dimethylsilyl-7-O-trimethyl-sily avermectin B1

38 mg of the product of Example 9 in 5 mL of tetrahydrofuran under nitrogen is combined with 30 mg of lithium bromide and the mixture is refluxed for 1 hour, cooled, and diluted with ether. The ether is washed several times with water, dried over sodium sulfate and concentrated to a small volume. The product is chromatographed on silica gel to afford 28 mg of the title compound, identified by nuclear magnetic resonance and mass spectrometry.

EXAMPLE 11

4-Methyl-4'',5-bis-O-tert butyl dimethylsilyl-7-O-trimethyl-silyl avermectin B1

30 μL of a 1.0M solution of sodium borohydride in dimethylformamide is added to a stirred solution of 38 mg of the product of Example 10 in 1.0 mL of dimethylformamide, and the reaction is monitored by silica gel thin layer chromatography. The addition is repeated until the starting material is absent, and ether is added to the mixture. The ether is washed several times with water, dried over sodium sulfate and the product is chromatographed on silica gel to afford 28 mg of the title compound, identified by nuclear magnetic resonance and mass spectrometry.

EXAMPLE 12

Avermectin B1

In a polypropylene vial, 35 mg of the product of Example 11 is combined with 3 mL of anhydrous hydrogen fluoride-pyridine-tetrahydrofuran prepared by mixing 0.3 mL of 70% hydrogen fluoride-pyridine, 0.9 mL of pyridine and 1.8 mL of tetrahydrofuran. After stirring at 20° for 2 days the mixtures is diluted with ether and washed several times with water. The product is chromatographed on silica gel to afford 15 mg of the title compound identified by nuclear magnetic resonance and mass spectrometry.

What is claimed is:

1. A compound having the formula:

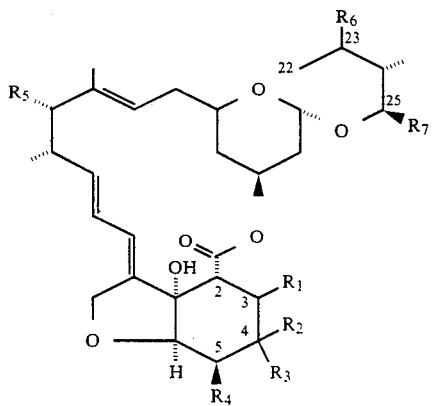

where $R_1$ is hydroxy or lower alkanoyloxy;
$R_2$ is hydroxy or lower alkanoyloxy and $R_3$ is hydroxymethyl or lower alkanoyloxy methyl; or
$R_2$ and $R_3$ together represent oxo or an epoxide;
$R_4$ is hydroxy, lower alkoxy, lower alkanoyloxy, oxo or oximino;
$R_5$ is hydrogen, hydroxy,

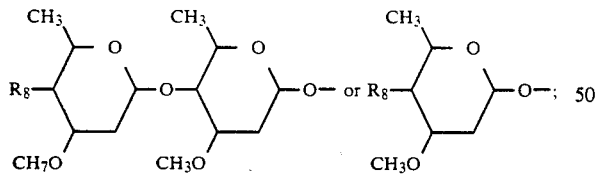

where $R_8$ is hydroxy, oxo, amino or mono- or di-substituted amino where the substituents are loweralkyl or lower alkanoyl;
$R_6$ is hydrogen, hydroxy or oxo and the broken line at the 22,23-position indicates a 22,23-single bond or the broken line at 22,23 indicates a 22,23-double bond and $R_6$ is not present; and
$R_7$ is lower alkyl or lower alkanoyl or cyclolower alkyl.

2. A compound of claim 1 wherein $R_1$ is hydroxy; $R_2$ is hydroxy and $R_3$ is hydroxy methyl; or
$R_2$ and $R_3$ together represent oxo or an epoxide;
$R_4$ is hydroxy, loweralkoxy oxo or oximino;
$R_5$ is hydrogen, hydroxy, or

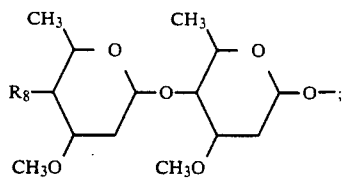

where $R_8$ is hydroxy, amino or mono- or di-substituted amino where the substituents are lower alkyl or lower alkanoyl;
$R_6$ is hydrogen or hydroxy and the broken line at 22,23- represents a 22,23-single bond; and
$R_7$ is lower alkyl.

3. A compound of claim 2 wherein $R_1$, $R_2$ and $R_3$ are as defined in claim 2;
$R_4$ is hydroxy, methoxy or oximino;
$R_5$ is

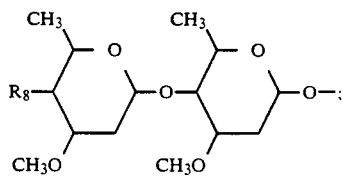

$R_8$ is hydroxy, amino, methylamino or acetylamino;
$R_6$ is as defined in claim 2; and
$R_7$ is isopropyl or sec-butyl.

4. A process for the preparation of a compound of claim 1 which comprises oxidizing with osmium tetroxide in benzene or toluene at from room temperature to 50° C. a compound having the formula:

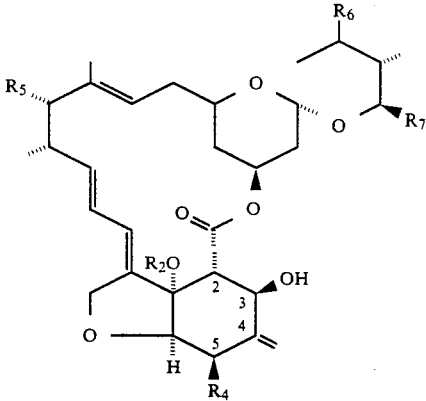

wherein $R_4$, $R_5$, $R_6$, $R_7$ and the 22,23-broken line are as defined in claim 1, to form the 4,4a-dihydroxy derivative;

oxidatively cleaving the 4,4a-dihydroxy compound with lead acetate in benzene or toluene at from 20° to 60° C. to form the 4-oxo derivative and the 2,3-4-oxo derivatives;

epoxidizing the 4-oxo derivative with a methylated oxo sulfonium methylide in methylene chloride, chloroform, THF or ether at room temperature to form the 4-epoxide;

preparing the loweralkanoyl derivative of the foregoing compounds with a loweralkanoyl anhydride or halide in an inert solvent in the presence of a base;

and recovering the desired product from the reaction mixture.

5. A process for the introduction of a $^{13}C$ or $^{14}C$ carbon atom at the 4a-position of an avermectin molecule which comprises oxidizing with osmium tetroxide in benzene or toluene at from room temperature to 50° C. a compound having the formula:

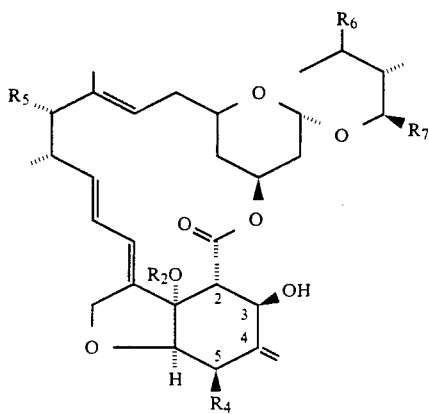

wherein $R_4$, $R_5$, $R_6$, $R_7$ and the 22,23-broken line are as defined in claim 1, to form the 4,4a-dihydroxy derivative;

oxidatively cleaving the 4,4a-dihydroxy compound with lead acetate in benzene or toluene at from 20° to 60° C. to form the 4-oxo derivative;

epoxidizing the 4-oxo derivative with a methylated oxo sulfonium methylide in methylene chloride chloroform, THF or ether at room temperature which incorporates a $^{13}C$ or $^{14}C$ carbon atom in the methylide portion of the reagent to form the 4-epoxide compound which incorporates the $^{13}C$ or $^{14}C$ carbon into the epoxide ring;

deoxygenating the epoxide with 3-methyl benzothiazole-2-selone in benzene at room temperature to form the 4-exomethylene with the $^{13}C$ or $^{14}C$ carbon atom at position 4a and; recovering the desired product from the reaction mixture.

6. The process of claim 5, wherein the radioactive carbon atom is $^{14}C$.

7. A method for the treatment of parasitic infections of animals which comprise treating an animal infected with parasites with an effective amount for the treatment of parasites of animals of a compound of claim 1.

8. A composition for the treatment of parasitic infections of plants or animals which comprises an effective amount for the treatment of parasites of animals or an effective amount for the treatment of parasites of plants of a compound of claim 1 and an inert carrier.

9. A method for the treatment of parasitic infections of plants which comprise treating a plant infected with parasites with an effective amount for the treatment of parasites of plants of a compound of claim 1.

* * * * *

UNITED STATES PATENT AND TRADEMARK OFFICE
CERTIFICATE OF CORRECTION

PATENT NO. : 5,240,915           Page 1 of 2
DATED     : August 31, 1993
INVENTOR(S) : Avery Rosegay It is certified that error appears in the above-indentified patent and that said Letters Patent is hereby corrected as shown below:

Delete the structural formulas in Column 4, lines 1-18 and in claim 1, column 17, lines 21-38, and replace the structural formulas with the following:

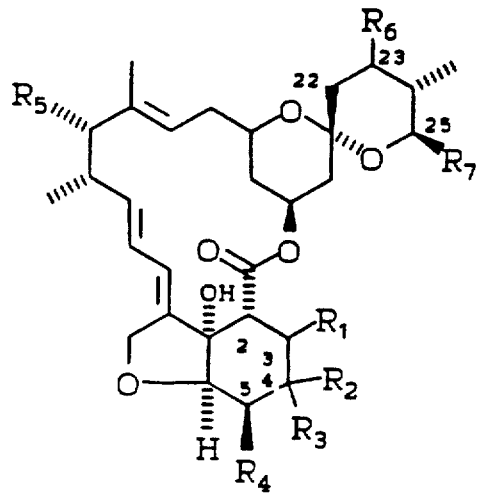

UNITED STATES PATENT AND TRADEMARK OFFICE
CERTIFICATE OF CORRECTION

PATENT NO. : 5,240,915
DATED : August 31, 1993
INVENTOR(S) : Avery Rosegay

It is certified that error appears in the above-indentified patent and that said Letters Patent is hereby corrected as shown below:

In claim 4, column 18, lines 37-53; and claim 5, column 19, lines 10-26, delete the structural formula and replace the structural formula with the following:

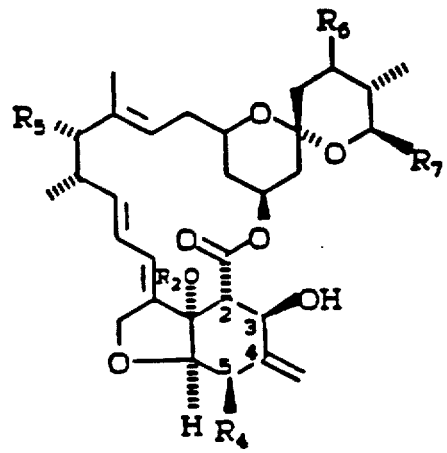

Signed and Sealed this

Twelfth Day of April, 1994

Attest:

BRUCE LEHMAN

Attesting Officer   Commissioner of Patents and Trademarks